United States Patent
Asakawa (10) Patent No.: US 10,188,974 B2
(45) Date of Patent: Jan. 29, 2019

(54) AGGREGATE-REMOVING FILTER MATERIAL, AGGREGATE REMOVAL METHOD, WHITE BLOOD CELL-REMOVING FILTER, AND BLOOD PRODUCT FILTERING METHOD

(71) Applicant: ASAHI KASEI MEDICAL CO., LTD., Tokyo (JP)

(72) Inventor: Masafumi Asakawa, Tokyo (JP)

(73) Assignee: ASAHI KASEI MEDICAL CO., LTD., Tokyo (JP)

(*) Notice: Subject to any disclaimer, the term of this patent is extended or adjusted under 35 U.S.C. 154(b) by 570 days.

(21) Appl. No.: 14/778,169

(22) PCT Filed: Mar. 18, 2014

(86) PCT No.: PCT/JP2014/057381
§ 371 (c)(1),
(2) Date: Sep. 18, 2015

(87) PCT Pub. No.: WO2014/148504
PCT Pub. Date: Sep. 25, 2014

(65) Prior Publication Data
US 2016/0279549 A1    Sep. 29, 2016

(30) Foreign Application Priority Data
Mar. 18, 2013   (JP) ................................. 2013-055138

(51) Int. Cl.
*B01D 39/00*   (2006.01)
*A61M 1/34*    (2006.01)
(Continued)

(52) U.S. Cl.
CPC ......... *B01D 39/163* (2013.01); *A61M 1/0281* (2013.01); *A61M 1/3496* (2013.01);
(Continued)

(58) Field of Classification Search
CPC ............ B01D 2239/00; B01D 2239/02; B01D 2239/0208; B01D 2239/0636;
(Continued)

(56) References Cited

U.S. PATENT DOCUMENTS

| 4,923,620 A | 5/1990 | Pall |
| 4,925,572 A | 5/1990 | Pall |

(Continued)

FOREIGN PATENT DOCUMENTS

| CN | 102006876 A | 4/2011 |
| JP | H1-236064 A | 9/1989 |

(Continued)

OTHER PUBLICATIONS

International Search Report issued with respect to application No. PCT/JP2014/057381, dated Jul. 1, 2014.
(Continued)

*Primary Examiner* — Allison G Fitzsimmons
(74) *Attorney, Agent, or Firm* — Greenblum & Bernstein, P.L.C.

(57) ABSTRACT

Provided are an aggregate-removing filter material enabling the efficient removal of aggregates while preventing the clogging by the aggregates, an aggregate removal method, a white blood cell-removing filter, and a blood product filtering method. An aggregate-removing filter material for removing aggregates in a blood product, which is composed only of fibers having a fiber length of 100 to 1000 mm, and a fineness of 0.7 to 4.0 dtex, and has a basis weight of 20 to 100 g/m$^2$, and a no-load bulk density of 0.03 to 0.10 g/cm$^3$.

20 Claims, 5 Drawing Sheets

(51) Int. Cl.
　　　*B01D 39/16* (2006.01)
　　　*A61M 1/02* (2006.01)
　　　*A61M 1/36* (2006.01)

(52) U.S. Cl.
　　CPC ... *A61M 1/3633* (2013.01); *A61M 2202/0439* (2013.01); *A61M 2205/7545* (2013.01); *B01D 2239/0627* (2013.01); *B01D 2239/1225* (2013.01); *B01D 2239/1233* (2013.01)

(58) Field of Classification Search
　　CPC ............ B01D 2239/1225; B01D 39/02; B01D 39/00; B01D 39/08; B32B 17/067
　　USPC ........... 210/767, 435, 445, 451, 456, 491.01
　　See application file for complete search history.

(56) References Cited

U.S. PATENT DOCUMENTS

| | | | |
|---|---|---|---|
| 4,976,861 | A | 12/1990 | Pall |
| 6,372,004 | B1 | 4/2002 | Schultink et al. |
| 2003/0162458 | A1 | 8/2003 | Tsujiyama et al. |
| 2004/0067710 | A1 | 4/2004 | Tsujiyama et al. |
| 2006/0073467 | A1 | 4/2006 | Kuno et al. |
| 2008/0233819 | A1 | 9/2008 | Tsujiyama et al. |
| 2011/0031191 | A1 | 2/2011 | Tatsuya et al. |

FOREIGN PATENT DOCUMENTS

| | | | |
|---|---|---|---|
| JP | H3-502094 | A | 5/1991 |
| JP | H3-173824 | A | 7/1991 |
| JP | H7-067958 | A | 3/1995 |
| JP | 2001-300222 | A | 10/2001 |
| JP | 2004-250795 | A | 9/2004 |
| JP | 2004250795 | A * | 9/2004 |
| JP | 2005-089870 | A | 4/2005 |
| JP | 2008-266828 | A | 11/2008 |
| JP | 2010-213820 | A | 9/2010 |
| JP | 2011-083312 | A | 4/2011 |
| KR | 2005-0024336 | A | 3/2005 |
| RU | 2 240 856 | C2 | 11/2004 |
| WO | 03/106518 | A1 | 12/2003 |
| WO | 2009-128435 | A1 | 10/2009 |

OTHER PUBLICATIONS

International Preliminary Report on Patentability issued with respect to application No. PCT/JP2014/057381, dated Oct. 1, 2015.
Yutaka Nagura et al., "Leukocyte-reduction filters and radiation do not cause significant changes in platelet function", Japanese Journal of Transfusion Medicine, vol. 49, No. 5, 2003, pp. 660-665.

* cited by examiner

| | EXAMPLES | | | | | | | | |
|---|---|---|---|---|---|---|---|---|---|
| | EXAMPLE 1 | EXAMPLE 2 | EXAMPLE 3 | EXAMPLE 4 | EXAMPLE 5 | EXAMPLE 6 | EXAMPLE 7 | EXAMPLE 8 | EXAMPLE 9 |
| FINENESS (DTEX) | 2 | 0.8 | 1.3 | 1.7 | 2.5 | 3.7 | 2 | 2 | 2 |
| BASIS WEIGHT (G/M²) | 80 | 80 | 80 | 80 | 80 | 80 | 30 | 80 | 80 |
| LONG FIBER CONTENT (%) | 100 | 92 | 100 | 100 | 100 | 100 | 100 | 94 | 80 |
| NO-LOAD BULK MM | 1.10 | 1.28 | 1.12 | 1.06 | 1.16 | 0.81 | 0.4 | 0.98 | 1.2 |
| NO-LOAD BULK DENSITY | 0.073 | 0.063 | 0.071 | 0.075 | 0.069 | 0.099 | 0.075 | 0.082 | 0.067 |
| HAVING COMPONENT IN BULK DIRECTION | ○ | ○ | ○ | ○ | ○ | ○ | ○ | ○ | ○ |
| THE NUMBER OF BLOCKS HAVING MOVEMENT IN BULK DIRECTION | 7 | 9 | 8 | 8 | 7 | 9 | 5 | 7 | 9 |
| EFFECTIVE FILTRATION PART (%) | 100 | 100 | 100 | 100 | 100 | 100 | 100 | 100 | 100 |
| ELONGATION (LONGITUDINAL) (MM) | 0.3 | 0.4 | 0.3 | 0.5 | 0.4 | 0.3 | 0.8 | 0.4 | 1.5 |
| ELONGATION (WIDTH) (MM) | 2.7 | 1 | 1 | 1.5 | 3.1 | 3.3 | 3.5 | 2.6 | 3.9 |
| ELONGATION PERCENTAGE (LONGITUDINAL) (%) | 0.15 | 0.20 | 0.15 | 0.25 | 0.20 | 0.15 | 0.40 | 0.20 | 0.75 |
| ELONGATION PERCENTAGE (WIDTH) (%) | 1.35 | 0.50 | 0.50 | 0.75 | 1.55 | 1.65 | 1.75 | 1.30 | 1.95 |
| ELONGATION RATIO (WIDTH / LONGITUDINAL) | 9 | 2.5 | 3.3333 | 3 | 7.75 | 11 | 4.375 | 6.5 | 2.6 |
| FALLING AMOUNT OF SHORT FIBERS | 5 THOUSAND | 20 THOUSAND | 10 THOUSAND | 8 THOUSAND | 4 THOUSAND | 3 THOUSAND | 3 THOUSAND | 8 THOUSAND | 20 THOUSAND FIBERS |
| FLOW RATE CHANGE RATIO | 87 | 77 | 77 | 73 | 73 | 65 | 60 | 79 | 75 |

Fig.3

| | COMPARATIVE EXAMPLES | | | | | | | |
|---|---|---|---|---|---|---|---|---|
| | COMPARATIVE EXAMPLE 1 | COMPARATIVE EXAMPLE 2 | COMPARATIVE EXAMPLE 3 | COMPARATIVE EXAMPLE 4 | COMPARATIVE EXAMPLE 5 | COMPARATIVE EXAMPLE 6 | COMPARATIVE EXAMPLE 7 | COMPARATIVE EXAMPLE 8 |
| FINENESS (DTEX) | 0.5 | 5 | 2 | 2 | 2 | 2 | 1.7 | 2 |
| BASIS WEIGHT (G/M²) | 80 | 80 | 15 | 110 | 80 | 40 | 40 | 30 |
| LONG FIBER CONTENT (%) | 100 | 100 | 100 | 100 | 50 | 38 | 0 | 100 |
| NO-LOAD BULK MM | 0.7 | 1.6 | 0.2 | 1.7 | 1.4 | 0.52 | 0.6 | 0.26 |
| NO-LOAD BULK DENSITY | 0.114 | 0.050 | 0.075 | 0.065 | 0.057 | 0.077 | 0.067 | 0.115 |
| HAVING COMPONENT IN BULK DIRECTION | ○ | ○ | ○ | ○ | ○ | ○ | ○ | × |
| THE NUMBER OF BLOCKS HAVING MOVEMENT IN BULK DIRECTION | 3 | 8 | 4 | 4 | 8 | 7 | 9 | 1 |
| EFFECTIVE FILTRATION PART (%) | 100 | 100 | 100 | 100 | 100 | 86 | 100 | 86 |
| ELONGATION (LONGITUDINAL) (MM) | 0.3 | 0.3 | 1.8 | 0.3 | 1.2 | 0.25 | 40 | 0.33 |
| ELONGATION (WIDTH) (MM) | 0.6 | 10 | 5.4 | 2.5 | 12 | 0.5 | 40 | 1.03 |
| ELONGATION PERCENTAGE (LONGITUDINAL) (%) | 0.15 | 0.15 | 0.90 | 0.15 | 0.60 | 0.13 | 20.00 | 0.17 |
| ELONGATION PERCENTAGE (WIDTH) (%) | 0.30 | 5.00 | 2.70 | 1.25 | 6.00 | 0.25 | 20.00 | 0.52 |
| ELONGATION RATIO (WIDTH / LONGITUDINAL) | 2 | 33.3333 | 3 | 8.333333 | 10 | 2 | 1 | 3.121212121 |
| FALLING AMOUNT OF SHORT FIBERS | 40 THOUSAND | 5 THOUSAND | 4 THOUSAND | 10 THOUSAND | 40 THOUSAND | 102 THOUSAND | 200 THOUSAND | 4 THOUSAND |
| FLOW RATE CHANGE RATIO | 43 | 46 | 45 | 47 | 78 | 73 | 70 | 30 |

Fig.4

Fig.5

AGGREGATE-REMOVING FILTER MATERIAL, AGGREGATE REMOVAL METHOD, WHITE BLOOD CELL-REMOVING FILTER, AND BLOOD PRODUCT FILTERING METHOD

TECHNICAL FIELD

The present invention relates to an aggregate-removing filter material, an aggregate removal method, a white blood cell-removing filter, and a blood product filtering method.

BACKGROUND ART

In recent years, in the field of blood transfusion, a blood transfusion before which mixed white blood cells contained in a blood product have been removed from the blood product, so-called leukapheresis has been spread. This is because it has been revealed that a relatively minor side effect such as headache, nausea, chill, and febrile nonhemolytic transfusion reaction, which are associated with blood transfusion, and a serious side effect such as alloantigen sensitization, viral infection, and graft versus host disease (GVHD) after blood transfusion, which may severely affect some blood recipients, are caused by the white blood cells mixed in the blood product that is used mainly for blood transfusion.

A method for removing white blood cells from a blood product is roughly divided into two types: a centrifugal separation method of separating and removing white blood cells by using a centrifugal separator utilizing the specific gravity difference between blood cell components; and a filter method of removing white blood cells by adhesion or adsorption using a filter material composed of a fiber assembly such as nonwoven fabric, a porous structure having continuous pores, or the like. Between them, the filter method of removing white blood cells by adhesion or adsorption is simply operated, and has an advantage of low cost, and the like, therefore, has been widely spread.

Many of the filter devices for removing white blood cells, which are currently available on the market, are constituted of multiple kinds of filter materials, and in the upstream close to an inlet port of blood, a coarse aggregate-removing filter material for removing aggregates of a blood product is arranged. Further, in the downstream part on the side of an outlet port, a fine white blood cell-removing filter material for removing white blood cells is arranged. The aggregate is made by the aggregation of a red blood cell, a white blood cell, a platelet, fibrin, fibrinogen, other denatured proteins, a fat globule, and the like.

The aggregate is present in the size of from around equal degree to that of a white blood cell in the smallest one to exceeding 1 mm in the largest one, and is enriched in adhesion. Further, as to the aggregate, there is a tendency that the longer the storage time of a blood product is, and/or the lower the storage temperature is, the larger the number of aggregates is, and the larger the size is. Therefore, when a blood product is treated only by a white blood cell-removing filter material without using an aggregate-removing filter material, there may be a case where the white blood cell-removing filter material is clogged with aggregates, and it becomes difficult to maintain the flow rate to be expected.

Further, in order to improve the quality of a blood product, white blood cell removal before storage, which performs the removal of white blood cells on the blood collection day or the next day after the blood collection, has become the mainstream. In recent years, in order to efficiently perform the white blood cell removal, the number of the facilities for performing the removal is reduced, and the number of the blood products treated in one facility is increased. In the facility, because a blood product is collected also from far away, the number of the bloods to be filtered after the refrigerated storage for one day is increased, therefore, the number of the bloods generating aggregates is also increased. Accordingly, during the filtration, flow failure is generated, and when the filtration is stopped, the blood product has to be discarded, therefore, the precious blood product is wasted. Therefore, there is a strong need for a filter to which an aggregate-removing filter material has been introduced.

In order to address such a problem, for example, in Patent Literature 1, a filter device having a structure in which in the upstream of a filter material for removing white blood cells, two or more kinds of the filter materials for removing aggregates, which are selected from the group consisting of nonwoven fabric, woven fabric, and knitted fabric, and have a bulk density different from each other in the range of 0.1 to 1.0 g/cm³, are arranged, and the bulk density of the aggregate-removing filter material is increased on the lower part of the downstream side has been disclosed.

In Patent Literature 2, a filter device composed of multiple kinds of fibrous materials, and defined by XY of an average fiber diameter X and an average fiber interval Y of fibers has been disclosed. This filter device has a structure in which a filter material of $XY>50$ is arranged in the upstream to capture larger aggregates, a filter material of $50 \geq XY>7$ is arranged in the downstream to capture relatively smaller aggregates, and a filter material of $7 \geq XY$ is arranged further in the downstream to remove white blood cells.

In Patent Literature 3, a filter material for removing aggregates in which there are at least two kinds of pore groups of a pore group A having the individual pore diameter of 500 µm or more, and a pore group B having the individual pore diameter of 150 to 500 µm, and the average pore diameter of the pore group A is 600 to 1500 µm, the average pore diameter of the pore group B is 200 to 450 µm, and the opening ratio is 40% or more has been disclosed.

In Patent Literature 4, a filter device in which the first to third elements are contained, and the first element is set as a filter material for removing gel (this is a synonym of a relatively large aggregate), the second element is set as a filter material for removing minute aggregates, and the third element is set as a filter material for removing white blood cells has been disclosed.

In Patent Literature 5, an aggregate-removing filter material composed of spunlace nonwoven fabric using short fibers has been disclosed. Further, In Patent Literature 6, an aggregate-removing filter material using base fabric of long fibers, and using short fibers has been disclosed.

CITATION LIST

Patent Literature

Patent Literature 1: Japanese Patent Application Laid-Open (JP-A) No. H03-173824

Patent Literature 2: JP-A No. H01-236064

Patent Literature 3: JP-A No. H07-67958

Patent Literature 4: Japanese Patent Application National Publication No. H03-502094

Patent Literature 5: JP-A No. 2010-213820
Patent Literature 6: International Publication WO 2009/128435

SUMMARY OF INVENTION

Technical Problem

The aggregate-removing filter materials, which have been disclosed in the above-described Patent Literatures 1 to 3, can be used without having any problems when a blood product containing a relatively small amount of aggregates is filtered. However, as to a blood product over long period of storage days, a blood product stored at a low temperature such a temperature of lower than 4° C., a blood product adjusted while the mixture of an anticoagulant agent and blood is insufficient after the blood collection, or the like, in a case where a blood product that is estimated to contain a relatively large amount of large aggregates is treated, the filtration flow rate is significantly decreased by the clogging. Further, there was a problem that filtration stops without being completed in many cases. In a case where the filtration time is drastically extended, an effective white blood cell removal area is decreased, and further the white blood cell removing performance may be decreased.

It is presumed that the reason why the problem of removing large-sized aggregates is left is that a fibrous shape aggregate-removing filter material used in Patent Literatures 1 to 3 has a dense structure, and a high bulk density. Such the filter material has a pore diameter smaller than the diameter of a large-sized aggregate having a size of several tens μm or more. Therefore, it is considered that when a blood containing large-sized aggregates is filtered, the aggregates remain in the vicinity of the surface of a filter material, and clogging is generated.

Further, the first element disclosed in Patent Literature 4 is called a needle fiber web, and is a needle fiber obtained by plunging a needle and mechanically interlacing fibers, and a nonwoven fabric using short fibers having a short fiber length. In the first element, the interlacement of fibers is not strong, therefore, with the situation as it is, elongation deformation, fracture, and the like may be generated. Therefore, the first element described in Patent Literature 4 is subjected to a pretreatment called hot compression at the time of filling into a filter device. By this hot compression, the shape of the first element can be held. However, there was a problem that ventilation resistance of a filter material becomes high by the hot compression, the resistance to the clogging by aggregates is decreased, and the performance is not stable.

The aggregate-removing filter material disclosed in Patent Literature 5 uses short fibers, therefore, there is a problem that the strength is low. In a case where the strength is low, there is a problem that the nonwoven fabric extends during the filter production and the resistance to the clogging is decreased, or shrinkage is generated in a sterilization process in which heat is added, the structure of nonwoven fabric becomes dense, and the resistance to the clogging is decreased. Further, in the aggregate-removing filter material composed of base fabric of long fibers, and of short fibers, which has been disclosed in Patent Literature 6, by increasing the basis weight of long fiber part, the strength can be enhanced, however, there is a problem that when the basis weight is excessively increased in order to obtain the sufficient strength, the interlacement of short fibers becomes difficult, and the aggregate resistance is not exerted. In addition, the performance degradation may be generated due to the falling of short fibers.

Further, in Patent Literatures 4 to 6, short fibers are used, however, generally short fibers are easy to fall off, therefore, there was a problem that when the short fibers are interlaced, the strength becomes weak, and the performance degradation is generated due to the falling of short fibers associated with the use, as a result of which the performance becomes unstable.

As described above, in the present situation, a filter material for removing aggregates, in which the resistance to the clogging by large-sized aggregates is high, and the strength is high and the performance is stable, has not been found.

An object of the present invention is to provide an aggregate-removing filter material, in which the resistance to the clogging by large-sized aggregates is high, and the strength is high and the performance is stable, and using the same, an aggregate removal method, a white blood cell-removing filter, and a blood product filtering method.

Solution to Problem

The aggregate-removing filter material according to one aspect of the present invention is an aggregate-removing filter material for removing an aggregate in a blood product, and is composed only of a fiber having a fiber length of 100 to 1000 mm and a fineness of 0.7 to 4.0 dtex, in which a basis weight is 20 to 100 g/m$^2$, and a no-load bulk density is 0.03 to 0.10 g/cm$^3$.

In one embodiment, a content of a fiber having a fiber length of 100 to 1000 mm may be 70% or more.

In one embodiment, a content of a fiber having a fiber length of 100 to 1000 mm may be 92% or more.

In one embodiment, a fineness of the fiber may be 1.3 to 2.4 dtex.

In one embodiment, the fiber may have a component in a bulk direction.

In one embodiment, in a case where a direction in parallel to the fiber is set as an x-axis, and a direction in a bulk direction of the fiber is set as a y-axis, a line is drawn at 250 μm intervals along each of the x-axis and the y-axis to make continuous 16 lattices, there may be four or more lattices, each of the lattices has the fiber having an angle between a lower line or upper line of the lattice and the fiber of 30 degrees or more, among the 16 lattices.

In one embodiment, an effective filtration area may be 90 to 100% of the total area.

In one embodiment, a value obtained by dividing elongation (%) in one direction of the fiber by elongation (%) in a direction perpendicular to the one direction of the fiber is 2 or more, and orientation may be provided in a plane direction.

In one embodiment, an elongation in a direction in which the elongation becomes the maximum may be 2% or less.

In one embodiment, an elongation in a direction perpendicular to a direction in which an elongation becomes the maximum may be 1% or less.

In one embodiment, the aggregate-removing filter material may be spunbonded nonwoven fabric produced by a spunbond process.

In one embodiment, the aggregate-removing filter material may be spunlace nonwoven fabric produced by a spunlace process.

In one embodiment, the fiber may be formed of polyester.

In one embodiment, the fiber may be formed of polyethylene terephthalate.

In one embodiment, a falling amount of fibers may be 100 thousand fibers/m² or less.

In one embodiment, a filtration flow rate at an end of filtration after 460 mL of a blood product has been filtered may be ensured by 50% or more of the filtration flow rate at a start of the filtration.

In one embodiment, a pressure loss at an end of filtration of 460 mL of a blood product may be twice or less of a pressure loss (Pa) at a start of the filtration.

The aggregate removal method according to one aspect of the present invention uses the above-described aggregate-removing filter material.

The white blood cell-removing filter according to one aspect of the present invention is composed of the above-described aggregate-removing filter material, and a white blood cell-removing filter material.

The blood product filtering method according to one aspect of the present invention uses the above-described white blood cell-removing filter.

Advantageous Effects of Invention

According to the present invention, aggregates can efficiently be removed while preventing the clogging by the aggregates.

DESCRIPTION OF EMBODIMENTS

Figure 1:
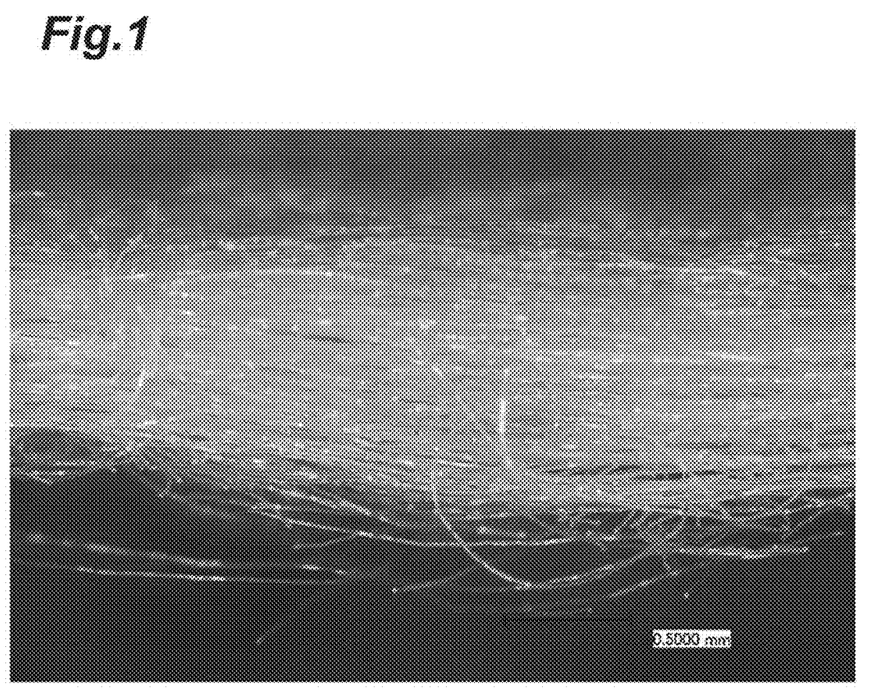
FIG. 1 is a picture showing the enlarged cross section of the aggregate-removing filter material according to one embodiment, that is, spunlace nonwoven fabric composed only of long fibers.

Hereinafter, the suitable embodiment of the present invention will be described in detail. FIG. 1 is a picture showing the enlarged aggregate-removing filter according to one embodiment, that is, spunlace nonwoven fabric composed only of long fibers. The aggregate-removing filter material shown in FIG. 1 is an aggregate-removing filter material for removing aggregates in a blood product. The aggregate-removing filter material is composed only of a fiber having a fiber length of 100 to 1000 mm and a fineness of 0.7 to 4.0 dtex, and has a basis weight of 20 to 100 g/m², and a no-load bulk density of 0.03 to 0.10 g/cm³. Further, the "blood product" described herein means various blood products used in blood transfusion, such as a whole blood preparation, a concentrated red blood cell preparation, and a concentrated platelet preparation. Hereinafter, the aggregate-removing filter material will be described in detail.

As described above, the fineness of the aggregate-removing filter material is 0.7 to 4.0 dtex. In a case where the fineness is less than 0.7 dtex, the meshes are extremely small, therefore, there is a tendency that the removal of the large-sized aggregates becomes difficult. On the other hand, in a case where the fineness exceeds 4.0 dtex, the entanglement of the fibers is decreased, and there is a tendency that the strength becomes insufficient. The fineness of the aggregate-removing filter material is preferably 1.0 to 3.0 dtex, and more preferably 1.3 to 2.4 dtex. In a case where the fineness is 1.3 dtex or more, the interlacement of the fibers is moderately dispersed, and large-sized aggregates are also easily removed, therefore, this is preferred. In a case where the fineness is 2.4 dtex or less, sufficient strength can be retained when the aggregate-removing filter material is used as a filter, therefore, this is preferred.

In addition, in the present embodiment, the "fineness" is a value determined by the length and weight of the fiber, defined in the Japanese Industrial Standards, JIS L0104 and JIS L1013. Further, in a case where the fiber is in an approximately cylindrical column shape, the fiber diameter is determined by the following procedures, and then the determined fiber diameter may be converted to the fineness by using a fiber density (g/cm³). As to the measurement of the fiber diameter, firstly, arbitrary five or more samples are obtained from a filter material, and pictures of the samples are taken by using a scanning electron microscope or the like at an adequate magnification at which the fiber diameter can be measured. Next, a lattice-like sheet was placed on the pictures, and the diameter of 100 or more of fibers at a lattice point is measured. The diameter herein, means the width of the fiber in a direction perpendicular to the fiber axis. The value (average value) obtained by dividing the sum of the diameters of the measured fibers by the number of fibers is set as the fiber diameter, and the "fineness" may be determined by using the value and the fiber density.

However, in a case where multiple fibers are overlapped each other, and the width cannot be measured by being hidden behind other fibers, or in a case where multiple fibers are being melted or the like, and become a thick fiber, and further, in a case where fibers having a diameter significantly different from each other, and the like, the obtained data are deleted. Further, in a case where multiple kinds of fibers having a diameter apparently different from each other are mixed, each fineness is determined from the average value of the respective fiber diameters, and in a case where the determined fineness is in the range of 0.7 to 4.0 dtex, the aggregate-removing filter material is included in the fiber of the present embodiment.

As the shape of the cross section that can be used for an aggregate-removing filter material, not only the round shape, but also any shapes can be used. For example, a modified cross-section structure as described in JP-A No. H08-170221, JP-A No. H08-291424, JP-A No. 2002-61023, JP-A No. 2004-225184, JP-A No. 2005-82939, or the like may also be used. However, from the viewpoint of the productivity of the fiber itself, a cross-section structure in a round shape is preferred.

The aggregate-removing filter material is composed only of fibers having a fiber length of 100 to 1000 mm. Being composed only of fibers having a fiber length of 100 to 1000 mm means that the proportion (content) of the fibers having a fiber length of 100 to 1000 mm is 70% or more. The proportion of fibers having a fiber length of 100 to 1000 mm is preferably 80% or more, more preferably 90% or more, and furthermore preferably 92% or more. When the proportion of fibers having a fiber length of 100 to 1000 mm is 92% or more, it is confirmed that the strength is extremely strong. In a case where the proportion of the fibers having a fiber length of 100 to 1000 mm is 94% or more, the cutting of fibers is less, and the falling of fibers becomes less, therefore, this is preferred. In a case where the proportion of the fibers having a fiber length of 100 to 1000 mm is 98% or more, short fibers are hardly contained, therefore, the changes in physical properties of nonwoven fabric, which are generated by the nap of the short fibers in a sterilization or production process, are not caused, therefore, the high performance can be exerted.

In a case where the aggregate-removing filter material has a fiber length of less than 100 mm, the fibers are easy to fall off, and there is a tendency that the resistance to clogging is decreased. On the other hand, in a case where the aggregate-removing filter material has a fiber length of 100 mm or more, the components in the bulk direction are decreased, and there is a tendency that the resistance to clogging is decreased. Further, the "fiber length" herein, is a value obtained by the measurement of the length of a fiber sampled by cutting nonwoven fabric into 20 cm×20 cm and arbitrarily pulling fibers out from the center part of the nonwoven fabric, utilizing an image analyzer, a ruler, or the like. However, a fiber cut at the time of the pulling out is not subjected to the measurement. The "proportion of fibers having a fiber length of 100 to 1000 mm" is a value obtained by performing the measurement of the fiber length of 50 fibers, by dividing the number of fibers having a fiber length of 100 to 1000 mm by the number of the measured fibers, and by multiplying by 100.

The aggregate-removing filter material composed only of fibers having a fiber length of 100 to 1000 mm can be obtained by processing nonwoven fabric composed only of long fibers with an appropriate method, and by cutting the nonwoven fabric into an adequate size to be used for a filter material. Therefore, in a case where nonwoven fabric that is produced by intentionally interlacing short fibers having a fiber length of around 1 to 80 mm with each other is used, the proportion of the fibers having a fiber length of shorter than 100 to 1000 mm is increased, therefore, the aggregate-removing filter material of the present invention cannot be obtained.

As one example, the one obtained by cutting the spunbonded nonwoven fabric produced by a spunbond process into an adequate size as a filter can be used. Further, the one obtained by performing other processing such as a spunlace method onto spunbonded nonwoven fabric can also be used. At this time, it has been known that fibers having a fiber length of 300 mm 1000 mm, or 500 mm 1000 mm are increased.

The aggregate-removing filter material has a basis weight of 20 to 100 g/m$^2$. In a case where the aggregate-removing filter material has a basis weight of less than 20 g/m$^2$, there is a tendency that the removal efficiency of aggregates is decreased and the insufficient strength is caused. On the other hand, in a case where the aggregate-removing filter material has a basis weight of exceeding 100 g/m$^2$, there may be a case where the filling into a filter device becomes difficult. Further, in a case where the basis weight exceeds 100 g/m$^2$, when the aggregate-removing filter material is filled into a filter device together with a filter material for removing white blood cells, and the like, there may be a case where a white blood cell-removing filter material is compressed, and the filtration flow rate of a blood product is decreased. The basis weight of the aggregate-removing filter material is preferably 40 to 90 g/m$^2$, and more preferably 70 to 90 g/m$^2$. Further, the "basis weight of a filter material" is determined, for example, by sampling three or more of parts from arbitrary parts having a size of 5 cm×5 cm and having the physical properties that seem to be uniform, by measuring the weight of each filter material to determine the average value, and by converting the average value to the weight per unit square meter.

The aggregate-removing filter material has a no-load bulk density of 0.03 to 0.10 g/cm$^3$. The no-load bulk density is more preferably 0.04 to 0.10 g/cm$^3$, and furthermore preferably 0.06 to 0.10 g/cm$^3$. In the aggregate-removing filter material, in a case where the no-load bulk density is less than 0.03 g/cm$^3$, the strength of nonwoven fabric becomes insufficient, and the aggregate removal performance is not stable. On the other hand, in the aggregate-removing filter material, in a case where the no-load bulk density is 0.10 g/cm$^3$ or more, the nonwoven fabric has a dense structure, and the aggregate removal performance is not provided. Further, the no-load bulk density is determined by dividing the basis weight by no-load bulk. The no-load bulk is the bulk of nonwoven fabric measured by the observation of the cross section of nonwoven fabric under atmospheric pressure by a microscope or an electron microscope, and the thickness is measured without loading. Specifically, the measurement was performed according to the following method. Firstly, nonwoven fabric is cut into a size of 5 cm×5 cm by scissors or the like so as not to apply pressure as much as possible, and three sides of the nonwoven fabric were fixed by a jig. Then, the one side that had not fixed was observed from a direction perpendicular to the cross section by a digital microscope (Type VHX-900, manufactured by KEYENCE), the thickness of three or more of parts from arbitrary parts of nonwoven fabric was measured, and the average value was determined.

Further, as to the aggregate-removing filter material incorporated in a filter that has been once formed, the no-load bulk is measured, and the no-load bulk density can be determined. At this moment, an aggregate-removing filter material taken out by dismantling a filter is left for around one hour, then the thickness of a part to which a rib and the like have not abutted at the forming of a filter (part having no history of deformation) is measured in the same manner as in the above, and the obtained value is set as no-load bulk. In addition, the thickness may vary as a result that a part of the aggregate-removing filter material has been pressed depending on the structure of a rib and the like inside the filter, however, it has been known that variation in the thickness in a part having no history of deformation before and after the filter formation is around 3%. Further, even if the filter material after the dismantlement of a filter is left for one hour or more, it has been confirmed that the variation in the thickness is hardly generated. Furthermore, when the basis weight is calculated, the volume of the nonwoven fabric is required, and using the value obtained by multiplying the area of the nonwoven fabric at this time by the no-load bulk obtained by the measurement according to the method described above as a volume, the weight (basis weight) per unit volume can be calculated.

The no-load bulk density of an aggregate-removing filter material in a filter after the formation is 0.03 to 0.10 g/cm$^3$, more preferably 0.04 to 0.10 g/cm$^3$, and furthermore preferably 0.06 to 0.10 g/cm$^3$.

One example of the production method of the aggregate-removing filter material described above will be described in detail. Firstly, chips of resin, which are to be a raw material, are heated and melted, and the molten resin is extruded from a nozzle having a certain diameter and directly spun. Next, the long fibers continuously spun without being cut are piled on a conveyor belt by overlapping a predetermined number of fibers, and formed into nonwoven fabric. The nonwoven fabric in this state is nonwoven fabric in a state of overlapping long fibers with each other, and the strength is insufficient. Therefore, by processing nonwoven fabric with a spunlace method, or a needle punch method, nonwoven fabric having strong strength can be produced.

The spunlace method is a method of interlacing long fibers of a synthetic polymer by high pressure water flow, and with which nonwoven fabric having bulkiness and extremely strong strength can be produced. Further, the needle punch method is a method of interlacing fibers by inserting a needle having a notch called barb to entangle fibers from the upper and lower, and nonwoven fabric having bulkiness and strong strength can be produced.

Further, when nonwoven fabric is processed by a spunlace method or a needle punch method, apart from a method of processing into long fibers immediately after the spinning, the nonwoven fabric to which a spunbond process has been processed in advance is wound once on a roll, and then may be processed by a spunlace method or a needle punch method. This method will be described in detail.

Firstly, chips of resin, which are to be a raw material, are heated and melted, and the molten resin was extruded from a nozzle having a certain diameter and directly spun. After that, the long fibers continuously spun without being cut are piled on a conveyor belt by overlapping a predetermined number of fibers, and formed into nonwoven fabric. Next, the nonwoven fabric is bonded onto a roll called a calender roll, and wound as spunbonded nonwoven fabric. Specifically, a calender roll having a pattern is heated to 120° C. to 200° C., and the nonwoven fabric is bonded onto a calender roll. At this moment, the heat and pressure to add to a calender roll are preferably adjusted weaker than those applying to ordinary spunbonded nonwoven fabric. By this procedure, the interlacement by water-flow interlacing or a needle is efficiently performed. By performing a spunlace method or a needle punch method to the thus produced spunbonded nonwoven fabric, nonwoven fabric having bulkiness and strong strength can be produced.

The aggregate-removing filter material produced according to the method described above is preferred as compared with that obtained by a production method of bonding fibers to each other, such as a thermal bond method, and a chemical bond method, because nonwoven fabric having a low bulk density can be prepared. The nonwoven fabric produced by the above-described processing method using a spunlace method or needle punch method of the present embodiment is possible to be made bulky as compared with spunbonded nonwoven fabric composed only of long fibers.

The above-described spunlace method will be described in detail. In the spunlace method, water is poured over nonwoven fabric and allowed to be blended before performing water-flow interlacing processing, as a result of which the amount of the water repelled by fibers at the time of water-flow interlacing is decreased, therefore, the efficiency of the water-flow interlacing is improved. Under the processing conditions of a processing speed at the processing of 3 to 20 m/min, a water pressure of 40 to 200 kgf/cm$^2$, a diameter of a nozzle spouting water of 80 to 150 μm, and a nozzle pitch of 0.5 to 2.0 mm, an intended filter material can be obtained.

In the spunlace method, when the processing speed at the processing is slower than 3 m/min, the productivity is decreased. On the other hand, in the spunlace method, when the processing speed is faster than 20 m/min, sufficient water-flow interlacing strength cannot be obtained. In the spunlace method, when the processing speed is made to be faster than 20 m/min, the number of nozzles is required to be increased to two to three nozzles in each of the upper and lower. The more preferred processing speed in the spunlace method is 4 to 15 m/min.

In the spunlace method, when the water pressure is lower than 40 kgf/cm$^2$, the interlacement does not sufficiently progress, and the required strength cannot be obtained. On the other hand, in the spunlace method, when the water pressure is higher than 200 kgf/cm$^2$, the cutting of fibers is generated, and the interlacement excessively progresses, as a result of which the bulk may be decreased. The more preferred water pressure in the spunlace method is 50 to 150 kgf/cm$^2$.

In the spunlace method, when the nozzle diameter is smaller than 80 μm, the pressure loss at a nozzle part becomes large, the required pressure becomes extremely high, therefore, the processing becomes difficult. On the other hand, in the spunlace method, when the nozzle diameter is larger than 150 μm, the pressure is decreased, therefore, the pressure required for the interlacement of fibers cannot be ensured. The more preferred nozzle diameter in the spunlace method is 90 to 140 μm.

In the spunlace method, when the nozzle pitch is 0.5 mm or less, the distance between the nozzle and the nozzle is short, therefore, the processing is difficult. On the other hand, in the spunlace method, when the nozzle pitch is larger than 2.0 mm, the water-flow interlacing part is decreased, and sufficient bulkiness and strength are not obtained. The more preferred nozzle pitch in the spunlace method is 0.7 to 1.8 mm, and more preferably 0.9 to 1.5 mm.

Further, nonwoven fabric, in which a content ratio of fibers having a fiber length of 100 to 1000 mm is 92% or more, can be produced by a production method using the above-described spunlace process. In the spunlace process, the production conditions are controlled so as to be a pressure of 40 to 150 kgf/cm$^2$, a nozzle diameter of 90 to 150 μm, and a pitch of 0.7 mm to 2.0 mm. As a result, the strength of water does not become the strength enough to cut fibers, therefore, the fibers are hardly cut in the production process, and nonwoven fabric, in which a content ratio of fibers having a fiber length of 100 to 1000 mm is high, can be produced.

The needle punch method will be described in detail. In the needle punch method, the processing speed is set to 3 to 50 m/min, and further a needle having a diameter of 0.5 to 2.0 mm is used. In the needle punch method, a needle having a triangular or star-shaped cross section is used, the number of barbs in each side is set to 1 to 3, the number of needlesticks per unit area is set to 30 to 500 holes/cm$^2$, and the depth of the needlestick is set to 5 to 15 mm, as a result of which the intended filter material can be obtained.

In the needle punch method, when the processing speed is slower than 3 m/min, the productivity is decreased. On the other hand, in the needle punch method, when the processing speed is faster than 50 m/min, in order to maintain the number of needlesticks per unit area in the range described above, multiple needle punching processing machines are required. Therefore, in the needle punch method, it is not preferred to increase the processing speed to be faster than 50 in/min. The more preferred processing speed in the needle punch method is 5 to 30 m/min.

In the needle punch method, when a needle having a diameter of smaller than 0.5 mm is used, the risk of needle breakage is increased, therefore, this is not preferred. On the other hand, in the needle punch method, when a needle having a diameter of larger than 2.0 mm is used, a needle hole remains on the nonwoven fabric after the needlestick. As a result, an aggregate flows through the needle hole onto the lower nonwoven fabric, and the lower nonwoven fabric may be clogged with the aggregate. The more preferred diameter of a needle in the needle punch method is 0.55 to 1.8 mm.

In the needle punch method, when the number of barbs in each side is zero, fibers are not interlaced with each other by needlestick, and the strength becomes insufficient. On the other hand, in the needle punch method, when the number of barbs in each side is four or more, the needle strength is decreased, and the risk of needle breakage is increased. The more preferred number of barbs in each side in the needle punch method is two to three.

In the needle punch method, when the number of needlesticks per unit area is set to less than 30 holes/cm$^2$, the interlacement strength becomes insufficient, as a result of which the strength as a fiber becomes insufficient. On the other hand, in the needle punch method, when the number of needlesticks per unit area is set to more than 500 holes/cm$^2$, the number of needlesticks becomes extremely large, and the long fiber is cut down, the strength is decreased, and further the risk of falling off the cut fibers is increased. The more preferred number of needlesticks per unit area in the needle punch method is 40 to 350 holes/cm$^2$, and more preferably 60 to 250 holes/cm$^2$.

In the needle punch method, when the depth of the needlestick is shallower than 5 mm, the interlacement does not progress, and sufficient strength as a fiber cannot be obtained. On the other hand, in the needle punch method, when the depth of the needlestick is deeper than 15 mm, the fibers interlaced by barbs are cut down, the strength is decreased, and further the risk of falling off the cut fibers is increased. The more preferred depth of the needlestick in the needle punch method is 6 mm to 13 mm, and more preferably 7 mm to 12 mm.

The explanation of the aggregate-removing filter material is returned. The fiber of the aggregate-removing filter material has a component in the bulk direction. Having a component in the bulk direction means a state of having fibers interlaced with each other in the bulk direction, and a fiber produced by a spunlace method or a needle punch method has a component in the bulk direction in many cases. On the other hand, the fiber produced by a melt blow method is composed only of a fiber in the surface direction in many cases, and it cannot be said that the fiber has a component in the bulk direction. The presence or absence of a component in the bulk direction can be examined quantitatively in the following method. Firstly, the cross section of nonwoven fabric is observed from a direction perpendicular to the cross section of the nonwoven fabric by a microscope, and the direction in parallel to the nonwoven fabric is set as an x-axis, and the bulk direction of the nonwoven fabric is set as a y-axis. Then, lines are drawn at 250 µm intervals respectively along the x-axis and the y-axis to prepare a lattice. Continuous 16 lattices are selected, and it is preferred that there are four or more lattices, each of the lattices has a fiber having an angle between a lower line or upper line of the lattice and the fiber of 30 degrees or more, among the 16 lattices. Further, it is preferred that there are seven or more lattices among the 16 lattices. Herein, the nonwoven fabric produced by a spunlace method or a needle punch method has four or more lattices among the 16 lattices in many cases, however, it is highly possible that the nonwoven fabric produced by a melt blow method does not have a component in the bulk direction, and the number of lattices is less than four lattices.

Specifically, the observation of a component in the bulk direction of nonwoven fabric was performed in the following method. Nonwoven fabric is cut into a size of 5 cm×5 cm, three sides of the nonwoven fabric were fixed by a jig, and the one side that had not fixed was observed from a direction perpendicular to the cross section of the nonwoven fabric by a digital microscope (Type VHX-900, manufactured by KEYENCE). After that, lines were drawn at 250 µm intervals respectively along both of the x-axis and the y-axis to prepare a lattice, continuous 16 lattices were selected, and a fiber in each lattice was observed.

Further, as to also the aggregate-removing filter material once formed into a filter, the presence or absence of a component in the bulk direction can be confirmed. At this time, the cross section is observed from a perpendicular direction by a digital microscope, and 16 lattices are selected in a part not deformed by the formation.

In the aggregate-removing filter material, the effective filtration area is 90 to 100% of a total area of the nonwoven fabric. In a case where the effective filtration area is less than 90%, the area where a liquid flows is decreased, and the sufficient aggregate resistance is not exerted. Further, the effective filtration area is an area of the colored part obtained by cutting nonwoven fabric into a size of 5 cm×5 cm, immersing the cut nonwoven fabric in red ink in around the amount of sufficiently soaking the cut nonwoven fabric therein, and confirming the cut nonwoven fabric in 10 minutes.

The fiber of the aggregate-removing filter material has orientation in a plane direction. Having orientation in a plane direction indicates that when considering two directions of a longitudinal direction and a width direction of a roll for nonwoven fabric, the value obtained by dividing the elongation (%) in the width direction by the elongation (%) in the longitudinal direction is 2 or more. That is, it means that the fibers are arranged in the longitudinal direction. In a case where fibers are arranged, when nonwoven fabric is processed while moving in the longitudinal direction of a roll for nonwoven fabric during the processing by a spunlace method or a needle punch method, the amount of the fibers captured by water flow or a needle is increased. Therefore, the interlacement of fibers easily proceeds, and higher aggregate removal performance comes to be provided as compared with the nonwoven fabric having less orientation.

It can be confirmed by obtaining the value of 2 or more, which is obtained by dividing the elongation (%) in one direction by the elongation (%) in a direction perpendicular to the one direction when considering two directions of one direction and a direction perpendicular to the one direction of the fiber, that the fiber of an aggregate-removing filter material has orientation in a plane direction. Further, the elongation in a direction in which the elongation of an aggregate-removing filter material becomes the maximum is preferably 2% or less, and the elongation in a direction perpendicular to the direction in which the elongation becomes the maximum is preferably 1% or less.

In the measurement of the elongation of a filter material, the produced filter material is cut into a width of 5 cm and a length of 30 cm, and three of the cut ones are prepared, and these were attached to an autograph universal testing machine (type AG-1, manufactured by Shimadzu Corporation). Then, the distance between chucks was set to 20 cm, the filter material was gradually pulled in the length direction, the distance between chucks was measured after the pulling with a force of 2N (0.4 N/cm), the average value was determined, and the elongation (%) was determined by the following equation (1).

$$((\text{Distance average value between chucks after loading}-10)/10-1) \times 100 (\%) \qquad (1)$$

The elongation is preferably 2% or less. In a case where the elongation is higher than 2%, the strength as a fiber is insufficient, the handling in a process is difficult, and the aggregate resistance cannot be stably exerted.

As the fiber used for the aggregate-removing filter material, a synthetic polymer is used as a material, and any one can be used without having any particular limitation as long as there is no effect on blood. Examples of the material include polyamide, polyester, polyacrylonitrile, polyurethane, polyvinyl formal, polyvinylacetal, polytrifluorochloroethylene, poly(meth)acrylate, polysulfone, polystyrene, polyethylene, polypropylene, cellulose, and cellulose acetate. Among them, polyester such as polyethylene terephthalate, and polybutylene terephthalate, which is particularly highly versatile, and easily interlaces fibers with each other by a needle punch or spunlace method, is preferred.

The aggregate-removing filter material having the constitution described above can prevent the clogging due to aggregates, and can efficiently remove the aggregates even if the object is a blood product containing relatively large aggregates in a large amount. Further, the low strength that becomes a problem in a conventional aggregate-removing filter material containing short fibers can be improved. This is because by using a fiber having a fineness and a fiber length, which are suitable for the present application, sufficient strength is imparted. As a result, the aggregate-removing filter material according to the present embodiment is even treated in various production processes of a water-washing treatment, a heat treatment, and the like, the changes in physical properties are not generated, and the stable production can be realized. Further, the changes in physical properties are small, therefore, the capturing performance of aggregates can be stabilized.

Further, in the aggregate-removing filter material according to the present embodiment, the falling of fibers is less, and the decrease of the performance in a filter production process can be suppressed. The aggregate filter has 100 million to 300 million fibers per square meter, and when the falling amount of fibers is 100 thousand fibers/m$^2$ or more, the structure is changed, and the aggregate removal performance is decreased. Therefore, the falling amount of fibers in a production process of an aggregate removing filter may be 100 thousand fibers/m$^2$ or less, and preferably 20 thousand fibers/m$^2$ or less. In the aggregate filter material processed by a spunlace method, in general, the falling amount of fibers is less, and the structure is stable, therefore, the decrease of the aggregate removal performance is hardly generated. On the other hand, in the aggregate-removing filter material processed by a needle punch method, the falling amount of fibers is large, and the structure is unstable, therefore, the aggregate removal performance is easily decreased.

Further, the description of "excellent in the resistance to the clogging by aggregates" means, for example, when a blood product containing aggregates is filtered by a filter, there is no significant difference between the flow rate (mL/min) at a start of the filtration, and the filtration flow rate (mL/min) at an end of the filtration of almost the whole amount of the blood product. More specifically, the description means the case where a filtration flow rate at an end of the filtration after 460 mL of a blood product has been filtered ensures 50% or more of the filtration flow rate at a start of the filtration. Preferably, the filtration flow rate at an end of the filtration is 70% or more, and more preferably, when the filtration flow rate is 80% or more, the decrease of the filtering speed can be suppressed.

Further, the description of "excellent in the resistance to the clogging by aggregates" means, in a case where it is assumed that the filtration is performed at a certain flow rate, a pressure loss at an end of the filtration of almost the whole amount of the blood product is not drastically increased as compared with the pressure loss at a start of the filtration. More specifically, the description means the case where the pressure loss at an end of the filtration of 460 mL of a blood product is twice or less the pressure loss (Pa) at a start of the filtration. The pressure loss at an end of the filtration is preferably 1.5 times or less. However, the blood product has an extremely large individual difference, and the height when the filtration is performed by a natural head, the flow rate in a case of a certain flow rate, and further the temperature of a blood product influence the filtration flow rate and the filtration pressure, therefore, as a guideline indicating the resistance to the clogging, these are intended to be shown herein.

When the aggregate-removing filter material of the present embodiment is arranged in the most upstream side of a blood filtration apparatus of a white blood cell-removing filter and the like, the clogging by large-sized aggregates is prevented, and the filtration of a blood product can be realized while maintaining the favorable flow rate. In general, the blood product of which the filtration has not been terminated has to be discarded, however, the aggregate-removing filter material of the present embodiment is excellent in the resistance to the clogging, therefore, the blood product having many aggregates, which has been an object to be discarded until now, can also be rescued. As a result, the present invention can significantly contribute to the effective use of a precious blood product, and becomes extremely useful also socially.

EXAMPLES

Hereinafter, the present embodiment will be described in more detail by way of Examples, however, the range of the present embodiment should not be limited by the following Examples.

Examples 1 to 8, and Comparative Examples 1 to 4

Spunbonded nonwoven fabric of long fibers composed of polyethylene terephthalate (PET) was produced by a method described above. Specifically, chips of PET were heated and melted, and the molten resin was extruded from a nozzle having a certain diameter and directly spun. After that, the long fibers continuously spun without being cut were piled on a conveyor belt and formed into nonwoven fabric. After that, while maintaining a state that a certain tension is applied to the long fibers, water at a pressure of 100 kgf/cm$^2$ was jetted from each of the upper nozzle and the lower nozzle, the fibers were interlaced with each other at a processing speed of 10 m/min, and various spunlace nonwoven fabrics having different basis weight, and different no-load bulk density were produced (Examples 1 to 8, and Comparative Examples 1 to 4). The diameter of the nozzle was set to 90 μm, and the pitch of the nozzles was set to 1.0 mm. For these samples, evaluation was performed by the measurement of the above-described elongation, the number of falling fibers, and a blood test.

[Count of the Number of Falling Fibers]

As to the number of falling fibers, firstly, a filter material cut into 5 cm×5 cm was left to stand in 500 mL of water. Then, the filter material was taken out in five minutes, and the water in which the filter material had been immersed was filtered through a membrane filter (black). After that, the membrane filter after the filtration was observed by a microscope or the like, and the number of falling fibers was counted. The obtained value was made to be 400 times, and the value was set to be the number of falling fibers per square meter.

[Blood Test]

A blood test was performed by the following procedures, and evaluation was performed by a flow rate change ratio. One sheet of the produced spunlace nonwoven fabric was prepared as an aggregate-removing filter material, and under the sheet, three sheets of the spunbonded nonwoven fabric made from polyethylene terephthalate, which has a fineness of 1.4 dtex and a basis weight of 30 g/m$^2$, were laminated. Further, under the sheet, two sheets of the melt-blown nonwoven fabric having a fineness of 0.03 dtex and a basis weight of 60 g/m$^2$, and 30 sheets of the melt-blown nonwoven fabric having a fineness of 0.016 dtex and a basis weight of 40 g/m$^2$ were laminated. The one thus produced was filled in a polycarbonate container having an inlet port and an outlet port of a blood product, and an effective filtration cross-sectional area of 45 cm$^2$ (6.7 cm×6.7 cm), and subjected to ultrasonic welding, and a white blood cell-removing filter device was produced. A filter material for removing aggregates was arranged on the side of the inlet port of blood, and a filter material for removing white blood cells was arranged on the side of the outlet port of blood.

Further, 400 mL of blood was collected into a blood bag in which CPD (56 mL) had been contained to obtain a whole blood preparation, and the preparation was stored in a refrigerator at 2° C. until aggregates were able to be confirmed. The thus prepared whole blood preparation containing aggregates was connected to a filter via a blood circuit having a clamp, and further in the downstream, a recovery bag for recovering the filtered blood product was attached. The recovery bag was placed on a balance, and filtration was performed at room temperature of 22±2° C. with a fall of 140 cm. For the resistance to the clogging by aggregates, the ratio (flow rate change ratio) of the flow rate in the filtration starting stage and the flow rate in the filtration ending stage was calculated.

[Flow Rate Change Ratio]

The collected blood in the blood bag was passed through a filter, and after the blood product reached the recovery bag, the time required until showing 50 g in the balance was measured, and the measured value was set to be a filtration initial flow rate (g/min). Further the filtration was continued, the time required for the increase of the blood product in the recovery bag from 350 g to 400 g was measured, and the measured was set to be a filtration final flow rate (g/min). The value obtained by dividing the filtration initial flow rate by the filtration final flow rate was calculated as the flow rate change ratio.

Figure 2:
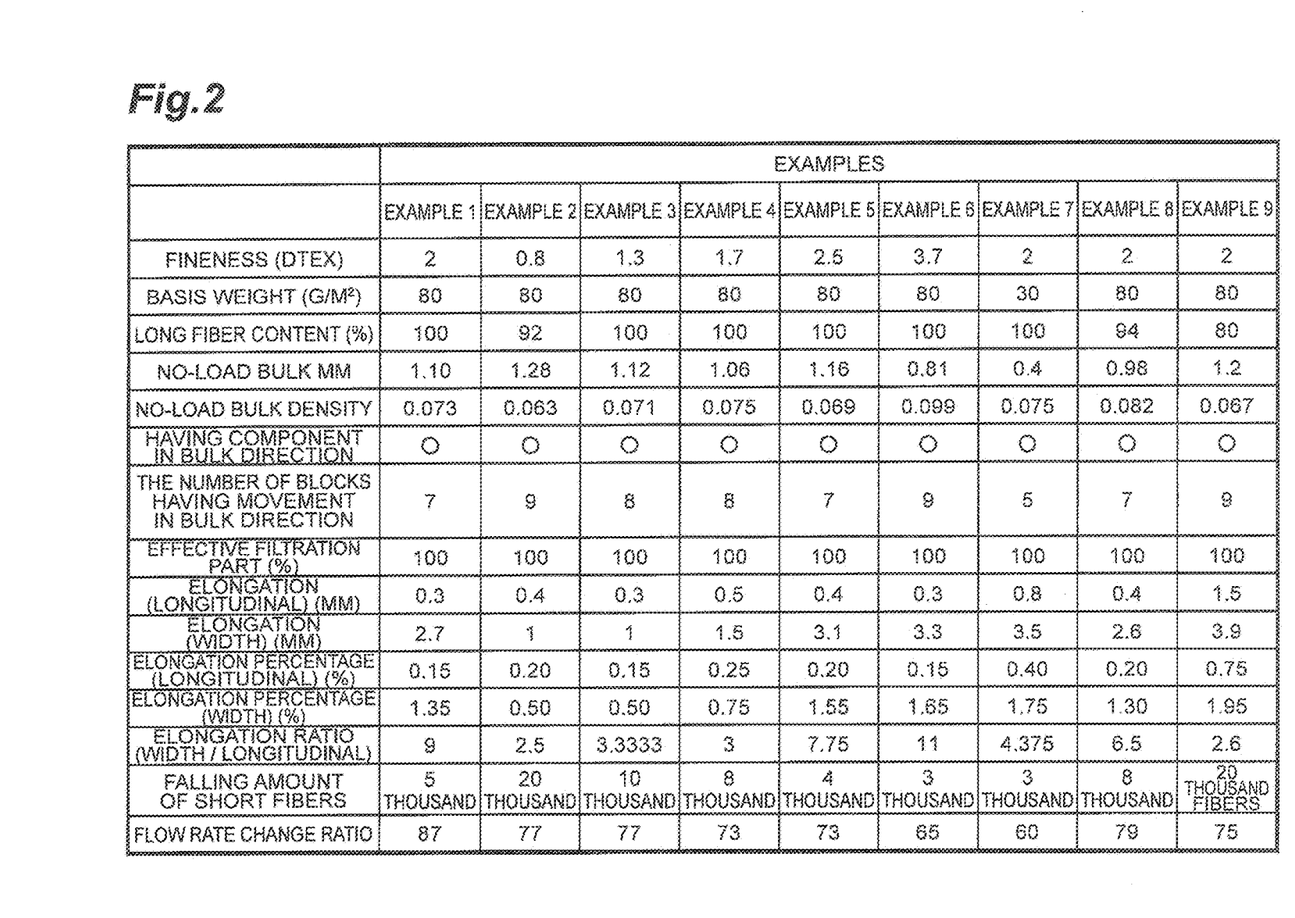
FIG. 2 is a table showing evaluation results.
Figure 3:
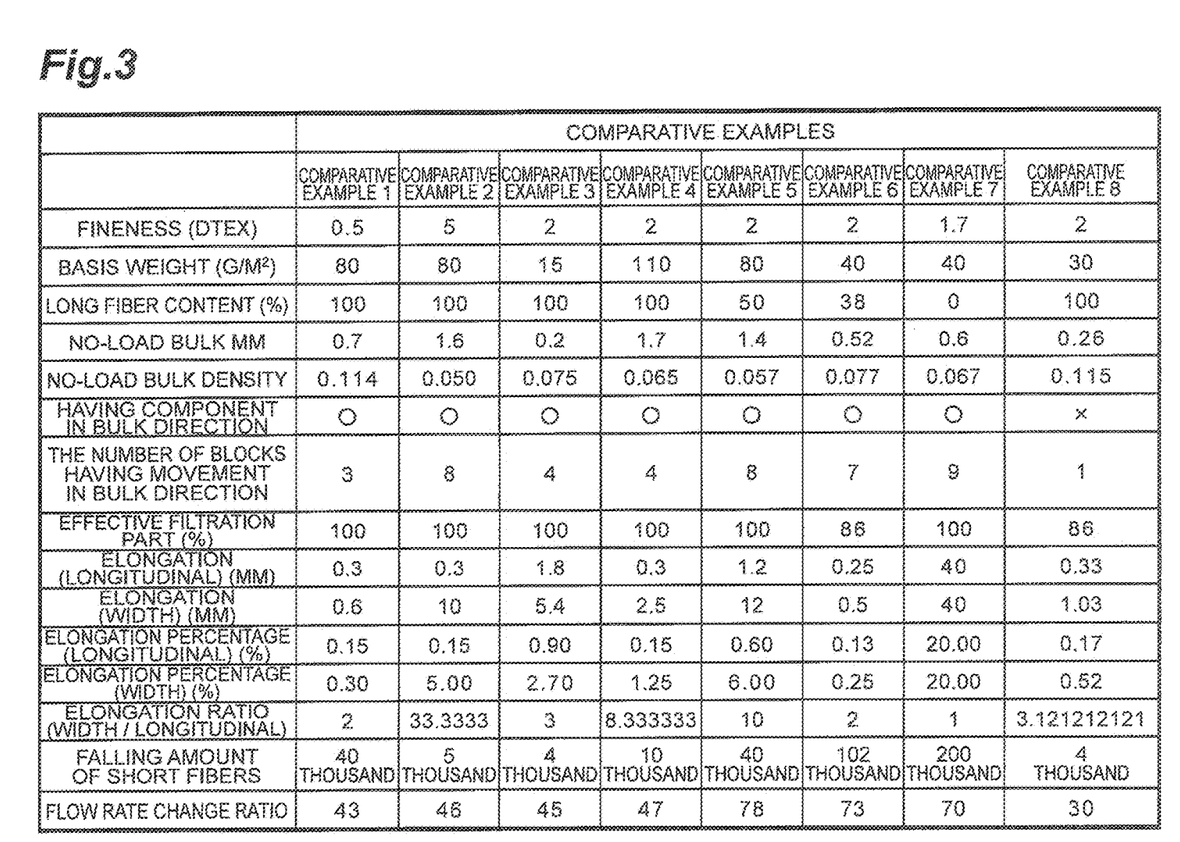
FIG. 3 is a table showing evaluation results.

Evaluation results of the characteristic values, and resistance to the aggregate clogging (flow rate change ratio) of the aggregate-removing filter material used in Examples 1 to 8 and Comparative Examples 1 to 4 were shown in FIG. 2 and FIG. 3. In all the experiments, any aggregates were not observed in the blood product after the filtration.

Example 9, and Comparative Example 5

Spunbonded nonwoven fabric of long fibers composed of polyethylene terephthalate (PET) was produced in the same manner as in Examples 1 to 8, and Comparative Examples 1 to 4. After that, while maintaining a state that a certain tension is applied to the long fibers, the fibers were subjected to a needle punching process and interlaced with each other at a processing speed of 5 in/min, and needle punched nonwoven fabric having a fineness of 2 dtex, and a different no-load bulk density was produced. In the needle punching process, a needle having a diameter of 0.5 mm, and a cross section of triangular with two barbs in each side was used, and the number of needlesticks per unit area was set to 100 holes/cm$^2$ in Example 9, and 600 holes/cm$^2$ in Comparative Example 5, and the depth of the needlestick was set to 10 mm. By using the needle punched nonwoven fabric, a white blood cell-removing filter device having the same constitution as that in Example 1 was produced, and filtration of a blood product was performed. As a result, the flow rate change ratio had the results shown in FIG. 2 and FIG. 3. Further, any aggregates were not observed in the recovery bag after the filtration.

Comparative Example 6

Spunbonded nonwoven fabric composed of long fibers having a basis weight of 15 g/m$^2$ composed of polyethylene terephthalate was produced. In the spunbonded nonwoven fabric, the temperature of calender rolls and the distance between the rolls were set to be different from those in Examples 1 to 8, and Comparative Examples 1 to 4. After that, base fabric was placed on a net, then on the base fabric, short fibers having a fineness of 1.7 dtex and a fiber length of 51 mm were placed at 25 g/m$^2$, and water at a pressure of 100 kgf/cm$^2$ was jetted from each of the upper nozzle and the lower nozzle at a processing speed of 5 m/min, as a result of which the fibers were interlaced with each other, and spunlace nonwoven fabric was produced. The diameter of the nozzle was set to 90 µm, and the pitch of the nozzles was set to 1.0 mm.

Figure 4:
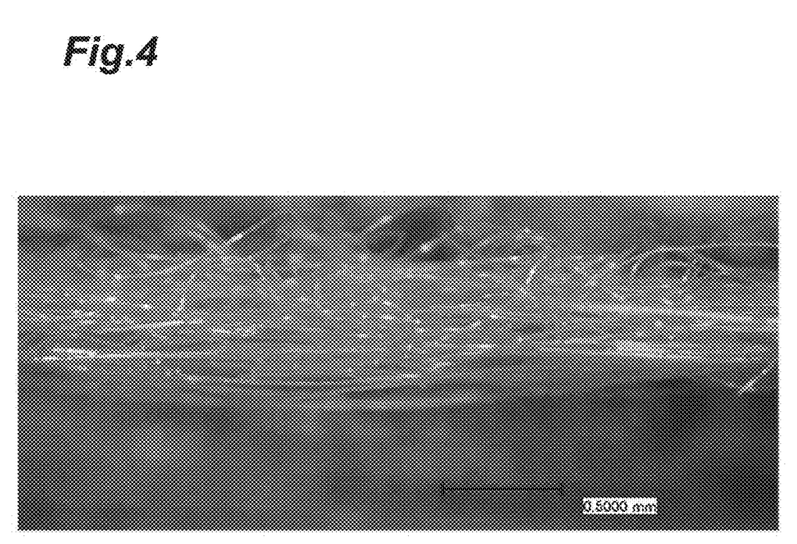
FIG. 4 is a picture showing the enlarged cross section of the spunlace nonwoven fabric composed of long fibers and short fibers.

The thus produced spunlace nonwoven fabric (an aggregate filter material) composed of long fibers and short fibers was shown in FIG. 4. FIG. 4 is a picture showing the enlarged cross section of the spunlace nonwoven fabric composed of long fibers and short fibers. By using the spunlace nonwoven fabric composed of long fibers and short fibers, a white blood cell-removing filter device having the same constitution as that in Example 1 was produced, and filtration of a blood product was performed. As a result, the flow rate change ratio had the results shown in FIG. 3, and the results were favorable. Any aggregates were not observed in the recovery bag after the filtration. However, the falling amount of short fibers was as many as 102 thousand fibers.

Comparative Example 7

Short fibers having a fineness of 1.7 dtex and a fiber length of 51 mm composed of polyethylene terephthalate were uniformly placed on a net at 40 g/m$^2$, and water at a pressure of 100 kgf/cm$^2$ was jetted from each of the upper nozzle and the lower nozzle at a processing speed of 5 m/min, as a result of which the fibers were interlaced with each other, and spunlace nonwoven fabric was produced. The diameter of the nozzle was set to 90 µm, and the pitch of the nozzles was set to 1.0 mm. By using the spunlace nonwoven fabric, a white blood cell-removing filter device having the same constitution as that in Example 1 was produced, and filtration of a blood product was performed. As a result, the flow rate change ratio had the results shown in FIG. 3, and the results were favorable. Any aggregates were not observed in the recovery bag after the filtration. However, both elongations in a longitudinal direction and in a width direction were 40 mm. Further, the falling amount of short fibers was as many as 20 thousand fibers.

Comparative Example 8

Figure 5:
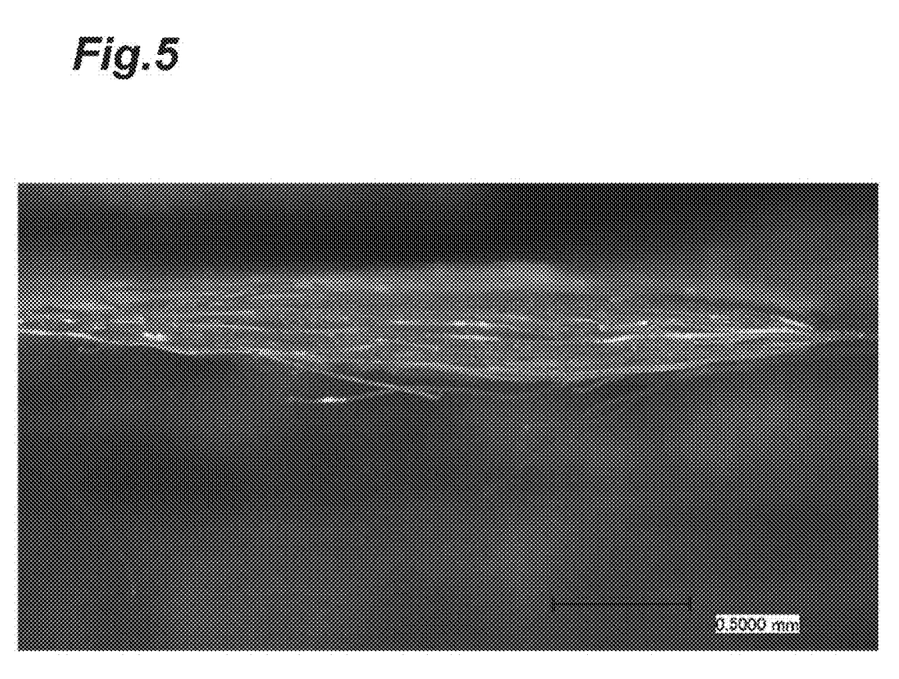
FIG. 5 is a picture showing the enlarged cross section of the spunbonded nonwoven fabric composed only of long fibers.

Spunbonded nonwoven fabric of long fibers composed of polyethylene terephthalate was produced. The spunbonded nonwoven fabric was produced as follows. A long fiber was spun by the extrusion of a molten resin, a conveyor belt was moved at 100 m/min, the basis weight was set to 30 g/m$^2$, and then part of fibers was melted and bonded by calender rolls at 130° C. The thus produced spunbonded nonwoven fabric (an aggregate filter material) composed of long fibers was shown in FIG. 5. FIG. 5 is a picture showing the enlarged cross section of the spunbonded nonwoven fabric composed of long fibers. By using the spunbonded nonwoven fabric composed of long fibers, a white blood cell-removing filter device having the same constitution as that in Example 1 was produced, and filtration of a blood product was performed. As a result, the flow rate change ratio was 30% as shown in FIG. 3, and the sufficient aggregate resistance was not exerted. Any aggregates were not observed in the recovery bag after the filtration. The falling amount of short fibers was as few as 4 thousand fibers.

INDUSTRIAL APPLICABILITY

The filter material for removing aggregates according to the present embodiment can be used in the fields: of medical industry, pharmaceutical industry, beauty industry, and the like.

The invention claimed is:

1. An aggregate-removing filter material for removing an aggregate in a blood product, the filter material consisting of fibers having a fineness of 0.7 to 4.0 dtex,
   wherein a basis weight of the filter material is 20 to 100 g/m2, a no-load bulk density of the filter material is 0.03 to 0.10 g/cm3, and at least 70% of the fibers have a fiber length of 100 mm to 1000 mm.

2. The aggregate-removing filter material according to claim 1,
   wherein at least 92% of the fibers have a fiber length of 100 mm to 1000 mm.

3. The aggregate-removing filter material according to claim 1,
   wherein the fineness of the fibers is from 1.3 to 2.4 dtex.

4. The aggregate-removing filter material according to claim 1,
   wherein the fibers have a component in a bulk direction.

5. The aggregate-removing filter material according to claim 4,
   wherein in a case where a direction in parallel to the fibers is set as an x-axis, and a direction in a bulk direction of the fibers is set as a y-axis, a line is drawn at 250 micron intervals along each of the x-axis and the y-axis to make continuous 16 lattices,
   there are four or more lattices, each of the lattices has the fibers having an angle between a lower line or upper line of the lattice and the fiber of 30 degrees or more, among the 16 lattices.

6. The aggregate-removing filter material according to claim 1,
   wherein an effective filtration area of the filter material is 90 to 100% of a total area of the filter material.

7. The aggregate-removing filter material according to claim 1,
   wherein a value obtained by dividing elongation (%) in one direction of the fibers by elongation (%) in a direction perpendicular to the one direction of the fibers is 2 or more, and orientation is provided in a plane direction.

8. The aggregate-removing filter material according to claim 1,
   wherein the filter material has a maximum elongation in a first direction in the plane of the filter material of 2% or less; whereby the maximum elongation in the first direction is determined by attaching a 20 cm span of a first 5 cm by 30 cm piece of the filter material to each of two chucks of a universal testing machine, the two chucks being spaced 20 cm apart at the attaching; subjecting the chucks with the filter material attached to a 2 N force pulling the chucks away from each other; measuring the distance between the chucks during the subjecting; and obtaining the percent elongation from the following Formula (1):

(((distance between the chucks during the subjecting−10)/10)−1)×100.

9. The aggregate-removing filter material according to claim 8,
   wherein the filter material has a maximum elongation in a second direction in the plane of the filter material of 1% or less, the second direction in the plane of the filter material being perpendicular to the first direction, whereby the maximum elongation in the second direction is determined by attaching a 20 cm span of a second 5 cm by 30 cm piece of filter material to each of two chucks of a universal testing machine, the 30 cm length of the second piece being perpendicular to the 30 cm length of the first piece, the two chucks being spaced 20 cm apart at the attaching; subjecting the chucks with the filter material attached to a 2 N force pulling the chucks away from each other; measuring the distance between the chucks during the subjecting; and obtaining the percent elongation from the following Formula (1):

(((distance between the chucks during the subjecting−10)/10)−1)×100.

10. The aggregate-removing filter material according to claim 1,
    wherein the aggregate-removing filter material is spunbonded nonwoven fabric produced by a spunbond process.

11. The aggregate-removing filter material according to claim 1,
    wherein the aggregate-removing filter material is spunlace nonwoven fabric produced by a spunlace process.

12. The aggregate-removing filter material according to claim 1,
    wherein the fibers are formed of polyester.

13. The aggregate-removing filter material according to claim 1,
    wherein the fibers are formed of polyethylene terephthalate.

14. The aggregate-removing filter material according to claim 1,
    wherein a falling amount of the fibers is 100 thousand fibers/m2 or less.

15. The aggregate-removing filter material according to claim 1,
    the filtering material having a first flow rate and a second flow rate, the first flow rate being determined from the lapsed time to filter the first 50 g of 460 mL of a blood product under a pressure and the second flow rate being determined from the lapsed time to filter the 350 g to the 400 g of 460 mL of the blood product under the same pressure, the second flow rate being half or more the first flow rate.

16. The aggregate-removing filter material according to claim 1,
the filter material having a first pressure and a second pressure, the first pressure determined from the average pressure to filter the first 50 g of 460 mL of a blood product at a flow rate and the second pressure determined from the average pressure to filter the 350 g to the 400 g of 460 mL of the blood product at the same flow rate, the second pressure being twice or less the first pressure.

17. An aggregate removal method comprising passing a blood product through an aggregate-removing filter material, the aggregate removing filter material consisting of fibers having a fineness of 0.7 to 4.0 dtex,
wherein a basis weight of the filter material is 20 to 100 g/m2, a no-load bulk density of the filter material is 0.03 to 0.10 g/cm3, and at least 70% of the fibers have a fiber length of 100 mm to 1000 mm.

18. A white blood cell-removing filter, comprising:
a white blood cell-removing filter material and
an aggregate-removing filter material, the aggregate-removing filter material consisting of fibers having a fineness of 0.7 to 4.0 dtex,
wherein a basis weight of the filter material is 20 to 100 g/m2, a no-load bulk density of the filter material is 0.03 to 0.10 g/cm3, and at least 70% of the fibers have a fiber length of 100 mm to 1000 mm.

19. A blood product filtering method comprising passing a blood product through a white blood cell-removing filter, the white blood cell-removing filter comprising:
a white blood cell-removing filter material and
an aggregate-removing filter material, the aggregate-removing filter material consisting of fibers having a fineness of 0.7 to 4.0 dtex,
wherein a basis weight of the filter material is 20 to 100 g/m2, a no-load bulk density of the filter material is 0.03 to 0.10 g/cm3, and at least 70% of the fibers have a fiber length of 100 mm to 1000 mm.

20. The aggregate-removing filter material according to claim 9, wherein the value obtained by dividing the maximum elongation in the first direction by the maximum elongation in the second direction is 2 or more.

* * * * *

UNITED STATES PATENT AND TRADEMARK OFFICE
CERTIFICATE OF CORRECTION

PATENT NO. : 10,188,974 B2
APPLICATION NO. : 14/778169
DATED : January 29, 2019
INVENTOR(S) : M. Asakawa It is certified that error appears in the above-identified patent and that said Letters Patent is hereby corrected as shown below:

In the Claims

Column 17, Line 38 (Claim 1) please change "g/m2" to -- $g/m^2$ --

Column 17, Line 39 (Claim 1) please change "cm3" to -- $cm^3$ --

Column 18, Line 63 (Claim 14) please change "m2" to -- $m^2$ --

Column 19, Line 23 (Claim 17) please change "g/m2" to -- $g/m^2$ --

Column 19, Line 24 (Claim 17) please change "cm3" to -- $cm^3$ --

Column 20, Line 7 (Claim 18) please change "g/m2" to -- $g/m^2$ --

Column 20, Line 8 (Claim 18) please change "cm3" to -- $cm^3$ --

Column 20, Line 18 (Claim 19) please change "g/m2" to -- $g/m^2$ --

Column 20, Line 19 (Claim 19) please change "cm3" to -- $cm^3$ --

Signed and Sealed this
Third Day of September, 2019

Andrei Iancu
*Director of the United States Patent and Trademark Office*